(12) United States Patent
Perkins et al.

(10) Patent No.: US 9,624,769 B2
(45) Date of Patent: Apr. 18, 2017

(54) DETERMINATION OF FLUID COMPOSITIONS

(71) Applicant: Halliburton Energy Services, Inc., Houston, TX (US)

(72) Inventors: David L. Perkins, The Woodlands, TX (US); Christopher Michael Jones, Houston, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 239 days.

(21) Appl. No.: 14/383,951

(22) PCT Filed: Nov. 11, 2013

(86) PCT No.: PCT/US2013/069400
§ 371 (c)(1),
(2) Date: Sep. 9, 2014

(87) PCT Pub. No.: WO2015/069290
PCT Pub. Date: May 14, 2015

(65) Prior Publication Data
US 2016/0237816 A1    Aug. 18, 2016

(51) Int. Cl.
*E21B 49/08*    (2006.01)
*G01N 21/27*    (2006.01)
(Continued)

(52) U.S. Cl.
CPC ........... *E21B 49/081* (2013.01); *G01N 21/27* (2013.01); *G01N 21/274* (2013.01); *G01N 21/85* (2013.01);
(Continued)

(58) Field of Classification Search
CPC ............. G01N 30/06; G01N 2030/042; G01N 2030/065; G01N 21/27; G01N 21/274;
(Continued)

(56) References Cited

U.S. PATENT DOCUMENTS 4,510,573 A    4/1985    Boyce et al.
5,723,861 A    3/1998    Carnahan et al.
(Continued)

FOREIGN PATENT DOCUMENTS

EP    1043583 A2    10/2000
EP    1043583 A3    4/2001
(Continued)

OTHER PUBLICATIONS

International Search Report and Written Opinion for PCT/US2013/069400 dated Aug. 7, 2014.
(Continued)

*Primary Examiner* — Daniel S Larkin
(74) *Attorney, Agent, or Firm* — McDermott Will & Emery LLP (57) ABSTRACT

A disclosed measurement system includes a fluid system that circulates a sample fluid exhibiting one or more unknown characteristics and being configured to receive a standard fluid that exhibits a known characteristic corresponding to at least one of the one or more unknown characteristics, an isolation cell fluidly coupled to the fluid system such that the sample fluid and a mixture of the sample fluid and the standard fluid are able to enter the isolation cell, an analyte-sensitive measurement device having one or more sensors associated therewith and being configured to analyze the sample fluid and the mixture and generate response signals corresponding to the one or more unknown characteristics of the sample fluid, and a signal processor configured to receive and perform standard addition calculations on the response signals in order to determine a concentration of the one or more unknown characteristics.

16 Claims, 2 Drawing Sheets

(51) Int. Cl.
*G01N 30/86* (2006.01)
*G01N 21/85* (2006.01)
*G01N 30/02* (2006.01)
*G01N 30/04* (2006.01)
*G01N 30/88* (2006.01)

(52) U.S. Cl.
CPC ....... *G01N 30/86* (2013.01); *G01N 2030/025* (2013.01); *G01N 2030/042* (2013.01); *G01N 2030/8854* (2013.01); *G01N 2201/12* (2013.01)

(58) Field of Classification Search
CPC .. G01N 21/85; G01N 30/86; G01N 2030/025; G01N 2201/12; E21B 49/081
USPC .............................................. 73/23.35, 23.41
See application file for complete search history.

(56) References Cited

U.S. PATENT DOCUMENTS

| | | |
|---|---|---|
| 7,317,516 B2 | 1/2008 | Treado et al. |
| 8,237,920 B2 | 8/2012 | Jones et al. |
| 2005/0170514 A1 | 8/2005 | Moore |
| 2007/0171412 A1 | 7/2007 | Vannuffelen et al. |
| 2008/0184810 A1* | 8/2008 | Kriz ................. G01N 27/40 73/861.08 |
| 2009/0071233 A1* | 3/2009 | Takahira ............. G01N 30/34 73/61.53 |
| 2010/0265509 A1 | 10/2010 | Jones et al. |
| 2012/0085149 A1 | 4/2012 | Al-Eid et al. |
| 2012/0232707 A1 | 9/2012 | Jones et al. |
| 2012/0272715 A1 | 11/2012 | Kriel et al. |
| 2013/0075093 A1 | 3/2013 | van Hal et al. |

FOREIGN PATENT DOCUMENTS

| | | | |
|---|---|---|---|
| WO | WO 2011/019355 | * | 2/2011 |
| WO | 2012078764 A2 | | 6/2012 |

OTHER PUBLICATIONS

Official Action for European Patent Application 14192432.4 dated Feb. 26, 2015.
Standard Addition, Wikipedia, Nov. 6, 2013, XP 055169624.
Saxberg et al., Generalized Standard Addition Method, Analytical Chemistry, American Chemical Society, vol. 51, No. 7, Jun. 1979, pp. 1031-1038, XP002689002.

* cited by examiner

DETERMINATION OF FLUID COMPOSITIONS

BACKGROUND

The present disclosure is related to fluid analysis and, more particularly, to using standard addition methods to determine fluid properties.

In the oil and gas industry, it can be important to precisely determine the characteristics and chemical compositions of fluids circulating into and out of subterranean hydrocarbon-bearing formations. Typically, the analysis of fluids related to the oil and gas industry is conducted off-line using laboratory analyses, such as spectroscopic, gas chromatography, and/or wet chemical methods, which analyze an extracted sample of the fluid. Off-line, retrospective analyses, however, can sometimes provide an inaccurate view of downhole fluids since the characteristics of an extracted sample of the fluid often change during the lag time between collection and analysis, thereby rendering the measured properties of the sample non-indicative of the true chemical composition or characteristic.

In some cases, the analyte of interest in the fluid sample may not be at a concentration high enough to be accurately measured with typical measurement systems. In such cases, for example, the analyte of interest in the fluid sample may be below the detection limits of various measurement devices associated with the measurement system. Accordingly, it may prove advantageous to employ a method that improves the limits of detection of low concentration analytes.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to fluid analysis and, more particularly, to using standard addition methods to determine fluid properties.

The embodiments disclosed herein describe the use of standard addition methods in order to determine fluid properties of a sample fluid in a measurement system. The standard addition methods increase the limits of detection for low concentration analytes or species found within the sample fluid. As a result, the disclosed embodiments improve sensor results that use simulated measurement systems as a base for a design of experiments for calibrations. Using standard addition methods may also minimize errors produced from flashing gas from the sample fluids. Those skilled in the art will readily recognize that flash effect errors are often one of the largest sources of errors in determining compositions of reservoir fluids. Accordingly, the disclosed embodiments may prove advantageous in providing increased control and accuracy in simulated measurement systems, which may then influence field and lab results that are vital in reservoir sampling. Moreover, the disclosed embodiments may prove advantageous in providing a means to undertake analytical measurements at a well site more rapidly than current methods.

Figure 1:
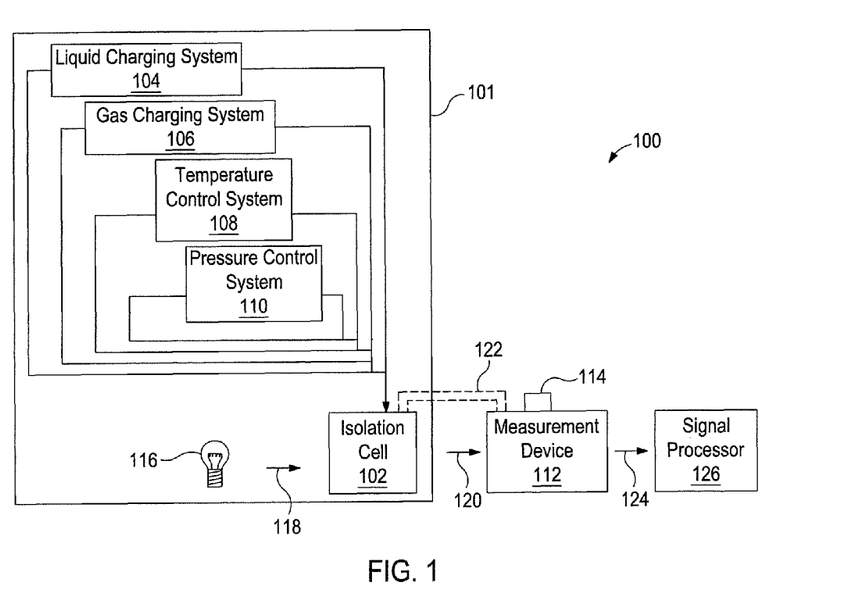
FIG. 1 is a measurement system that may employ the principles of the present disclosure, according to one or more embodiments.

Referring to FIG. 1, illustrated is a measurement system 100 that may employ the principles of the present disclosure, according to one or more embodiments. The measurement system 100 may be configured to circulate one or more sample fluids in a fluid system 101 over varying conditions of temperature, pressure, density, chemical concentration (i.e., gas-oil-ratio (GOR)), etc., such that the detection of one or more characteristics of each sample fluid may be made at such conditions. As used herein, the term "measurement system" refers to any closed-system apparatus or instrument capable of circulating one or more fluids, varying the conditions (e.g., temperature, pressure, density, chemical concentration, etc.) of such fluids, and measuring characteristics or properties of such fluids at the varied conditions while at controlled or non-controlled conditions. In some embodiments, the measurement system 100 may be an optical pressure-volume-temperature (PVT) instrument, generally known to those skilled in the art. In other embodiments, however, the measurement system 100 may encompass a cuvette, or the like.

The sample fluids circulated in the fluid system 101 may include fluids that are being tested to determine fluid properties or characteristics associated therewith. In some embodiments, one or more of the sample fluids may be a liquid. In other embodiments, however, one or more of the sample fluids may be a gas or a mixture of a gas and a liquid, without departing from the scope of the disclosure. In some embodiments, the sample fluids may be extracted samples of downhole reservoir fluids, such as fluids commonly found in the exploration and production of hydrocarbons in the oil and gas industry. For instance, the sample fluids may include fluids that contain representative spectroscopic absorptions of components commonly found in downhole fluids. In other embodiments, the sample fluids may be any fluid where it may be beneficial or desired to determine one or more fluid properties or characteristics associated therewith. For instance, the measurement system 100 may be useful in determining fluid properties or characteristics for fluids in fields or industries including, but not limited to, the food and drug industry, industrial applications, and mining industries.

As used herein, the term "characteristic" refers to a chemical, mechanical, or physical property of the sample fluid and may include a quantitative or qualitative value of one or more chemical constituents or compounds present therein or any physical property associated therewith. Such chemical constituents and compounds may be referred to herein as "analytes." Illustrative characteristics of a sample fluid that can be measured with the measurement system 100 described herein can include, for example, chemical composition (e.g., identity and concentration in total or of individual components), phase presence (e.g., gas, oil, water, etc.), fluid quality (e.g., % gas in a gas or a liquid, or % liquid in a liquid-solid mixture), impurity content, pH, alkalinity, viscosity, density, ionic strength, total dissolved solids, salt content (e.g., salinity), opacity, bacteria content, total hardness, combinations thereof, state of matter (solid, liquid, gas, emulsion, mixtures, etc.), and the like.

As mentioned above, the measurement system 100 may be configured to vary the operating conditions (i.e., temperature, pressure, density, and GOR) of sample fluids as they circulate therein. To accomplish this, as illustrated, the fluid system 101 may include a liquid charging system 104, a gas charging system 106, a temperature control system 108, and a pressure control system 110. In some embodiments, the sample fluids may be "dead" fluids, such as laboratory samples from which most of the volatiles and gases have escaped or "flashed" from the fluid. The liquid and gas charging systems 104, 106 may be configured to charge the sample fluids as they circulate in order to simulate "live" fluids, or fluids that will typically be found in a downhole environment. For example, in some embodiments, the liquid charging system 104 may inject another fluid (either dead or live) into the circulating sample fluids in order to introduce fluid perturbations configured to supply the sample fluid with typical or expected compounds or analytes. In one embodiment, for instance, a sample fluid may be charged or otherwise diluted with toluene as injected by the liquid charging system 104.

Similarly, the gas charging system 106 may be configured to inject a known gas into the circulating sample fluids to vary or otherwise regulate the GOR of each sample fluid to differing degrees. Not unlike the liquid charging system 104, this may be done to perturb the sample fluid, but this may also be done to re-inject volatiles back into the "dead" sample fluid and thereby more accurately simulate a specific type of downhole fluid. Exemplary gases that may be injected into the sample fluids via the gas charging system 106 include, but are not limited to, $N_2$, $CO_2$, $H_2S$, methane, propane, ethane, butane, combinations thereof, and the like. Each of these compounds are low-boiling gases that typically escape or "flash" from downhole fluids during the sampling process. As can be appreciated, the amount of gas injected into the sample fluid via the gas charging system 106 may vary depending on what GOR is to be simulated in the measurement system 100 in order to meet a particular condition or GOR set point.

The temperature control system 108 may be configured to vary the temperature of the sample fluid in order to simulate several temperature points commonly encountered downhole. To accomplish this, the temperature control system 108 may include or otherwise encompass one or more of an oven, a heat exchanger, a heating element, or any device configured to regulate the temperature of a fluid. Similarly, the pressure control system 110 may be configured to vary the pressure of the sample fluid in order to simulate several pressure points commonly encountered downhole. To accomplish this, the pressure control system 110 may include or otherwise encompass one or more compressors, pumps, and/or valves that serve to regulate the pressure of the sample fluid.

The measurement system may further include an isolation cell 102 fluidly coupled to each of the systems 104, 106, 108, and 110 such that each sample fluid is able to flow through or otherwise be captured within the isolation cell 102. In some embodiments, the sample fluids may be able to circulate through the isolation cell 102 and back to each of the systems 104, 106, 108, and 110 in a continuous, closed-loop circuit. In other embodiments, a small volume or portion of the sample fluid may be extracted and introduced into the isolation cell 102 for analysis. As will be appreciated, several valves, conduits, and other known fluid coupling devices are not specifically shown in FIG. 1 but are nonetheless included in the fluid system 101 in order to facilitate the closed-loop circuit.

The fluid system 101 and, more particularly, the isolation cell 102, may be operably coupled to an analyte-sensitive measurement device 112 configured to take measurements of the sample fluid. The analyte-sensitive measurement device 112 may include or otherwise encompass any known device or apparatus used to analyze a sample fluid and determine one or more fluid properties, analytes, or characteristics associated therewith. As illustrated, the analyte-sensitive measurement device 112 may include one or more detectors 114 associated therewith and configured to monitor the sample fluid. In some embodiments, for example, the analyte-sensitive measurement device 112 may be a gas or liquid chromatograph or the like. In other embodiments, the analyte-sensitive measurement device 112 may be a spectrometer (e.g., a Fourier transform infrared spectrometer (FTIR) or a grating monochromator), a densitometer, a viscometer, a nuclear resonance spectrometer, an electrochemical cell (e.g., scanning voltammetry, coulometry, and potentiometric methods), and any combination thereof, including combinations of analytic methods and detectors.

In yet other embodiments, the analyte-sensitive measurement device 112 may be an optical computing device or "opticoanalytical device." Such optical computing devices will often employ an optical processing element that optically interacts with the sample fluid to determine quantitative and/or qualitative values of one or more physical or chemical properties thereof. The optical element may be, for example, an integrated computational element (ICE), also known as a multivariate optical element (MOE). One type of ICE is essentially an optical interference filter that can be designed to operate over a continuum of wavelengths in the electromagnetic spectrum from the UV to mid-infrared (MIR) ranges, or any sub-set of that region. Electromagnetic radiation that optically interacts with the sample fluid is changed and filtered by the ICE so as to be readable by the detector 114, such that an output of the detector 114 can be correlated to the physical or chemical property of the fluid sample being analyzed.

As used herein, the term "operably coupled" can refer to a physical or optical communication between the isolation cell 102 and the analyte-sensitive measurement device 112. In some embodiments, for example, such as in the case of a gas chromatograph, the isolation cell 102 may be in fluid communication with the analyte-sensitive measurement device 112 such that a portion of the sample fluid may be extracted and analyzed by the analyte-sensitive measurement device 112. In other embodiments, such as in the case of a spectrograph or an optical computing device, the isolation cell 102 may be in optical communication with the analyte-sensitive measurement device 112 such that the analyte-sensitive measurement device 112 may optically interact with the sample fluid. As used herein, the term "optically interact" refers to the reflection, transmission, scattering, diffraction, or absorption of electromagnetic radiation either on, through, or from the sample fluid.

In embodiments where the analyte-sensitive measurement device 112 is a spectrograph or optical computing device, the isolation cell 102 may define or otherwise provide an internal fluid flow path fluidly coupled to each system 104, 106, 108, and 110 and extending between two transparent windows made of, for example, glass, plastic, semi-conductors, crystalline materials, polycrystalline materials, hot or cold-pressed powders, combinations thereof, or the like. During circulation, the sample fluid flows through the flow path and a light source 116 may be configured to emit electromagnetic radiation 118 that passes through the transparent windows of the isolation cell 102 and the sample fluid flowing therethrough. The light source 116 may be, for example, a light bulb, a light emitting diode (LED), a laser, a blackbody, a photonic crystal, an X-Ray source, a flame, combinations thereof, or the like. As the electromagnetic radiation 118 passes through the isolation cell 102 it optically interacts with the sample fluid and generates sample interacted light 120. The sample interacted light 120 may include spectral data for the particular sample fluid circulating through the fluid system 101 at the given conditions. The sample interacted light 120 may be directed toward the analyte-sensitive measurement device 112 to be analyzed.

In embodiments where the analyte-sensitive measurement device 112 is a gas chromatograph, a portion of the fluid sample may instead be conveyed to or otherwise accessed by the gas chromatograph via a conduit or channel 122. The channel 122 may be configured to fluidly communicate the isolation cell 102 with the gas chromatograph so that characteristics of the fluid sample may be detected or otherwise measured in the analyte-sensitive measurement device 112.

The one or more detectors 114 associated with the analyte-sensitive measurement device 112 may be any sensor capable of generating a response signal 124 corresponding to a characteristic of the sample fluid. In some embodiments, for example, the detector 114 may be any device capable of detecting electromagnetic radiation, and may be generally characterized as an optical transducer. The detector(s) 114 may include, but is/are not limited to, a thermal detector (e.g., a thermopile or photoacoustic detector), a semiconductor detector, a piezo-electric detector, a charge coupled device (CCD) detector, a video or array detector, a split detector, a photon detector (such as a photomultiplier tube), photodiodes, combinations thereof, or the like, or another detector known to those skilled in the art.

In some embodiments, for example, the detector 114 may be any device capable of measuring the gases from the gas chromatograph. The detector(s) 114 may be, but is/are not limited to, a thermal conductivity detector (TCD), or a flame ionization detector (FID), a catalytic combustion detector (CCD), a discharge ionization detector (DID), or the like, or another detector known to those skilled in the art.

The response signal 124 produced by the analyte-sensitive measurement device 112 (e.g., the detector(s) 114) may be a voltage, a current, a pressure pulse, or other waveform, and may be conveyed to and otherwise received by a signal processor 126 that is communicably coupled to the analyte-sensitive measurement device 112 or the detector(s) 114. The signal processor 126 may be a computer including a non-transitory machine-readable medium. In real-time or near real-time, the signal processor 126 may be configured to determine or otherwise calculate the concentration or magnitude of the characteristic of interest in the sample fluid.

In some embodiments, however, the concentration of the characteristic or analyte of interest in the sample fluid may be too small to be accurately detected by the sensor 114. In such cases, a standard fluid may be introduced into the fluid system 101 at a known volume and exhibiting a known characteristic of interest. The standard fluid may be a gas or a liquid and may be introduced via the liquid charging system 104 and/or the gas charging system 106. In some embodiments, the standard fluid may be a pure gas or a pure fluid, such as methane, ethane, hexane, etc., and may have a known concentration of a characteristic or analyte of interest.

The standard fluid may mix with the sample fluid in the isolation cell 102 such that any measurements taken of the sample fluid with the analyte-sensitive measurement device 112 may reflect the addition of the standard fluid. The signal processor 126 may then be configured to undertake one or more mathematical operations on the response signals 124 generated by the analyte-sensitive measurement device 112. For instance, the signal processor 126 may be configured to perform standard addition calculations on the response signals 124 in order to improve the limits of detection for the sensor 114, such that the concentration of the characteristic or analyte of interest in the sample fluid may be generally determined. The standard addition methods and calculations employed by the signal processor 126 and contemplated herein are generally disclosed in the examples provided below.

If the analyte-sensitive measurement device 112 is an optical spectrometer, then the signal processor 126 may be configured to generate a base spectrum of intensity of the signal versus its wavelength. In other words, the spectrometer may be configured to monitor multiple wavelengths or may be tuned to a single optical wavelength for a specific analyte or characteristic. In at least one embodiment, the wavelengths monitored by the spectrometer may result in a change in the response signal 124 as the standard fluid is added to the fluid system 101. This, in turn, could result in a change of absorption of the mixture as a function of wavelength or from a change in scattering of light within the observed path length.

In embodiments where the analyte-sensitive measurement device 112 is an optical computing device, one or more ICE components could be used to monitor one or many of the analytes or characteristics present in the sample fluid. In such embodiments, the one or more ICE components may be designed or otherwise manufactured to be sensitive the analytes or characteristics of interest that may be present in the sample fluid. As the standard fluid is added to the fluid system 101, the response signals 124 will reflect an increase in the analytes or characteristics of interest.

In embodiments where the analyte-sensitive measurement device 112 is a gas chromatograph, the standard fluid (i.e., "GC standard") introduced into the fluid system 101 would result in an increase in the peak area for the specific analyte or characteristic of interest. Additionally, a mixture of GC standards may be added to the sample fluid to affect multiple peak areas. The difference(s) between the peak area for the resulting mixture (i.e., the sample fluid plus the GC standard(s)) and the peak area for the GC standard (run previously) may provide the user with the concentration of the analyte within the untreated or original sample fluid.

As will be appreciated, if the standard fluid is the same as one of the analytes or characteristics of interest contained in sample fluid, the response signal 124 generated by the analyte-sensitive measurement device 112 will yield a positive calibration sensitivity, or the slope of a plot of the signal versus concentration, for that analyte. However, if the standard fluid is not the same as one of the analytes or characteristics of interest contained in sample fluid, the calibration sensitivity would be negative and thereby reflect a dilution of the analyte or characteristic of interest in the sample fluid. Accordingly, the disclosed methods may prove advantageous in optimizing the injection standard for specific analytes at parts-per-billion compounds of unknown sample fluids.

The disclosed methods may also prove advantageous in determining or otherwise analyzing the matrix effects present in the measurement system 100 for multi-compound injections (i.e., generalized standard addition). As used in this disclosure, "matrix" refers to components or analytes of fluids other than the chemical analyte of interest in a sample fluid. For example, when investigating asphaltenes in reservoir fluids, it is understood that the nature of the type of reservoir fluid can impact the measurement. The matrix may have a considerable effect on the way an analysis is conducted and the quality of the results obtained.

To facilitate a better understanding of the present disclosure, the following examples of representative embodiments are given. In no way should the following examples be read to limit, or to define, the scope of the disclosure.

In this first example, the disclosed methods may be used to improve the limits of detection for low concentration analytes or characteristics of interest in a sample fluid. For instance, it may be desired to know the concentration ($c_x$) of a characteristic of interest present within a fluid, such as a fluid extracted from a subterranean formation. To determine this unknown concentration ($c_x$), a known total volume ($V_t$) of the fluid may be injected into the fluid system 101 as a sample fluid, as generally described above. If desired, the fluid system 101 may operate to vary the operating conditions of the sample fluid in order to simulate a predetermined operating condition for the sample fluid.

Figure 2:
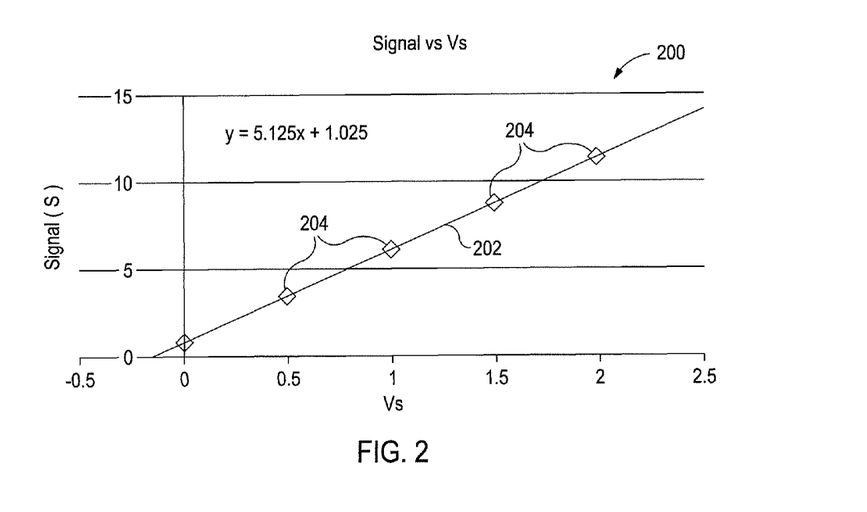
FIG. 2 depicts a plot of the signal response versus the volume of added standard fluid, in accordance with an example of an embodiment of the present disclosure.

With the known total volume ($V_t$) circulating in the fluid system 101, a first measurement of the sample fluid may be made and recorded using the analyte-sensitive measurement device 112. A known volume ($V_s$) of a standard fluid may then be injected into the fluid system 101 and mix with the sample fluid. The standard fluid may have or otherwise exhibit a known concentration ($c_s$) of the analyte or characteristic of interest. At this point, a second measurement of the sample fluid, including the addition of the standard fluid, may be made and recorded using the analyte-sensitive measurement device 112. The response signal 124 (S) detected by the sensor 114 may be described as follows:

$$S=(kV_sc_s)/V_t+(kV_xc_x)/V_t \qquad \text{Equation (1)}$$

where k is a proportionality constant, and $V_x$ represents the known volume of the analyte in a sample. The standard fluid may then be injected or otherwise added to the fluid system 101 at one or more additional sequential points in time to develop a calibration for the measurement system 100. Each addition of the standard fluid is made at a known volume ($V_s$). FIG. 2 depicts a plot 200 of the signal (S) versus the known volumes ($V_s$) of several sequential standard fluid additions, thereby rendering a calibration curve 202. As illustrated, four additions 204 of 0.5 (arbitrary units) have been added to the fluid system 101 and the signal (S) correspondingly increases with each addition. It will be appreciated that more or less than four additions of the standard fluid may be made, without departing from the scope of the disclosure.

The slope (m) and intercept (b) of the calibration curve 202 may then be calculated using the following equations:

$$m=(kc_s)/V_t \qquad \text{Equation (2)}$$

$$b=(kV_xc_x)/V_t \qquad \text{Equation (3)}$$

The intercept (b) is the signal (S) that would be recorded at the sensor 114 if no standard fluid were added to the fluid system 101. Both (m) and (b) may be determined using a least squares fit to the data recorded by the sensor 114. The unknown concentration ($c_x$) may then be calculated by taking the ratio of (b) and (m) in conjunction with known quantities $c_s$, $V_x$, and $V_s$:

$$(b/m)=((kV_xc_x)/V_t)/(kc_s)/V_t)=(V_xc_x)/c_s \qquad \text{Equation (4)}$$

$$c_x=(bc_s)/(mV_x) \qquad \text{Equation (5)}$$

Alternatively, the plot of signal (S) versus known volume ($V_s$) can be extrapolated to the x-axis intercept $V_s(0)$. In other words, the x-intercept represents the volume of standard fluid when the signal (S) at the sensor 114 is equal to zero. Therefore, Equation (1) above may be set equal to zero in order to solve for $C_x$ as follows:

$$c_x=(-(V_s(0))*c_s)/V_x \qquad \text{Equation (6)}$$

Now that the unknown concentration ($c_x$) of the characteristic of interest originally present within the sample fluid is known, a new plot of S versus composite fluid concentration ($c_m$) may be generated at each addition of the known concentration ($c_s$) using the following:

$$c_m=(V_sc_s+V_xc_x)/V_t \qquad \text{Equation (7)}$$

Figure 3:
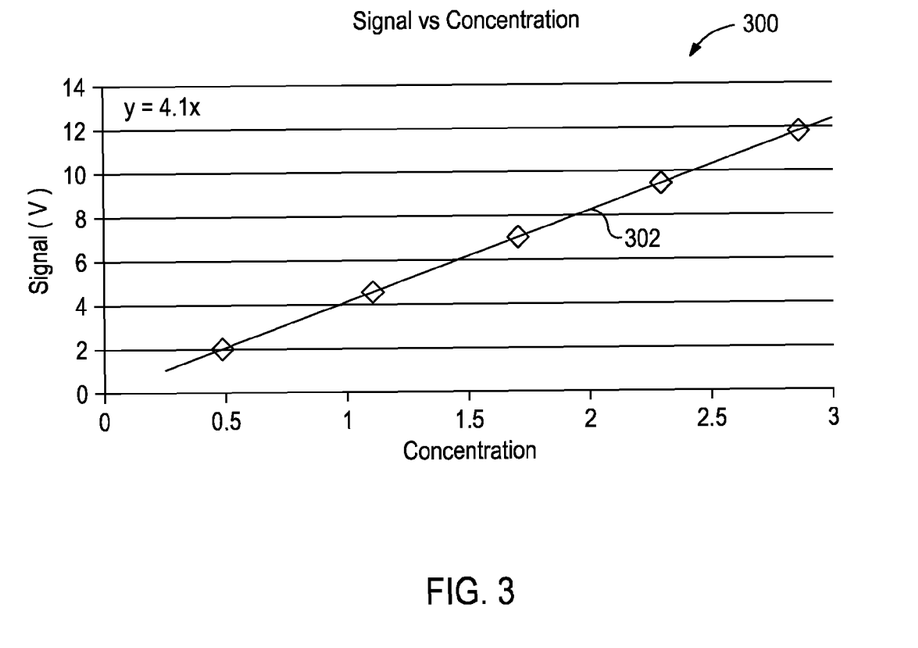
FIG. 3 depicts a plot of the signal response versus the concentration of added standard fluid, in accordance with an example of an embodiment of the present disclosure.

This is shown in the plot 300 FIG. 3 and the associated calibration curve 302, where the slope of S versus $c_m$ is k (equal to 4.1 in FIG. 3) from Equation (1) above, and the intercept is equal to zero. At this point, the measurement system 100 has been calibrated and any future unknown concentrations ($c_x$) of the sample fluid may be calculated using the following:

$$c_x=S/k \qquad \text{Equation (8)}$$

As will be appreciated, the signal processor 126 may be programmed and otherwise configured to perform the standard addition mathematical operations of Equations (1)-(8) such that the future unknown concentrations ($c_x$) of sample fluids may be determined.

In a second example, the disclosed methods may be used to mitigate flash effect errors common to fluid extracted from subterranean formations. To extract fluids from a subterranean formation, one or more sample containers may be conveyed downhole to target locations and opened to allow the influx of a sample of the surrounding reservoir fluid present at that location within the wellbore. These sample reservoir fluids often undergo a change in temperature and pressure in the sample containers as they are collected, transported to the surface, and subsequently analyzed. These changes in temperature and pressure may cause the fluid properties to change from their initial in-situ conditions. For example, temperature changes may cause precipitation of solids out of solution, and pressure changes may cause a gas or gases to come out of solution. It is difficult to ascertain how much gas remains in the liquid phase or otherwise how much gas flashes off. These types of changes can result in inaccurate measurements of the extracted fluids due to an inaccurate sampling of the fluid concentrations.

According to the present methods, and with continued reference to Equations (1)-(8) above, it may be possible to charge the measurement system 100 containing the sample fluid with a known standard fluid, flash the mixture of the sample fluid and the standard fluid, and then apply standard addition methods to ascertain the amount of gases initially flashed from the sample fluid. A known volume ($V_x$) of the fluid may be injected into the fluid system 101 as a sample fluid, as generally described above. If the sample fluid is a "dead" fluid, one or more reference or standard fluids may be injected into the sample fluid in order to simulate components in the fluid that would have been present in the downhole environment. Moreover, using the temperature and pressure control systems 108, 110, the sample fluid may then be brought to and maintained at a desired temperature and pressure. The desired temperature and pressure may be configured to simulate downhole conditions for the sample fluid.

With the known total volume ($V_t$) circulating in the fluid system 101, at known temperatures and pressures, a first measurement of the sample fluid may be made and recorded using the analyte-sensitive measurement device 112. A small volume of the sample fluid may then be removed from the fluid system 101 and flashed (e.g., a partial flash of the sample fluid) under controlled conditions. The gases that flash out of the small volume of the sample fluid may then be captured and also measured using the analyte-sensitive measurement device 112. The measurement of the flashed gases may be a single-phase measurement of the small volume of extracted sample fluid and may indicate the concentrations ($c_s$) of analytes (e.g., methane, ethane, butane, etc.) present in the flashed gases, and thus what was present in the sample fluid prior to extraction.

A known volume ($V_s$) of a standard fluid may then be injected into the fluid system 101 and mixed with the sample fluid. In some embodiments, the known volume ($V_s$) may be the same volume as the small volume of the sample fluid removed from the fluid system 101 and subsequently flashed. In other embodiments, however, the known volume ($V_s$) may different, without departing from the scope of the disclosure. The standard fluid may be a pure fluid injected into the fluid system 101 in order to alter the concentration of an analyte or characteristic of interest for the sample fluid. In some embodiments, the standard fluid may be a gas chromatograph standard fluid (a "GC standard"), which contains 36 different hydrocarbon components, ranging from $C_1$ to $C_{18}$. Accordingly, the standard fluid may exhibit a known concentration ($c_s$) of the analyte or characteristic of interest for the sample fluid.

At this point, a second measurement of the sample fluid, including the addition of the standard fluid, may be made and recorded using the analyte-sensitive measurement device 112. The response signal 124 (S) detected by the sensor 114 may be ascertained according to Equation (1) above. Another small volume of the sample fluid may then be removed from the fluid system 101 and flashed (e.g., a partial flash of a portion of the sample fluid and the additional standard fluid). The gases that flash out of the small volume mixture may then be captured and also measured using the analyte-sensitive measurement device 112. The measurement of these flashed gases may again indicate the concentrations ($c_s$) of analytes (e.g., methane, ethane, butane, etc.) present in the flashed gases, and thus what was present in the sample fluid prior to extraction.

The standard fluid may then be injected or otherwise added to the fluid system 101 at one or more additional sequential points in time to develop a calibration for the measurement system 100. Each addition of the standard fluid is made at known volumes ($V_s$), such that the slope (m) and intercept (b) of a resulting calibration curve (e.g., calibration curve 200 of FIG. 2) may be determined and the unknown concentration ($c_x$) of the characteristic of interest originally present within the sample fluid may then be calculated using one of Equations (5) and (6) above. At this point, the measurement system 100 has been calibrated and any future unknown concentrations ($c_x$) of a sample fluid may be calculated using Equation (8). Again, as indicated above, the signal processor 126 may be programmed and otherwise configured to perform the standard addition mathematical operations of Equations (1)-(8).

Accordingly, when a user introduces a sample of a fluid having an unknown concentration ($c_x$) of the analyte of interest into the measurement system 100, the calibration curves 200, 300 of FIGS. 2 and 3, respectively, generated by the standard addition methods described herein may be used to accurately determine the concentration. With reference to FIG. 3, where the resulting signal (S) of sample fluid falls on the calibration curve 300, a vertical line may be drawn to the x-axis to provide the user with the particular concentration of the analyte of interest.

Moreover, once the concentration of the analyte of interest is determined, the volume of gas added to the fluid system 101 may also be determined. For example, the signal versus concentration plot 300 of FIG. 3 and Equation (7) may be used to determine the volume of an added reference gas ($V_s$) if the concentration of the added reference gas is accurately known. If the fluid circulating in the fluid system 101 has a known volume ($V_x$) and concentration ($c_x$), and a reference fluid ($c_s$) is added to the fluid system 101, the signal (S) of the resulting mixture will change proportionally to the amount of reference fluid added ($V_s$). Using the signal (S) of the mixture in FIG. 3, the composite fluid concentration ($c_m$) can be determined. Moreover, if the change in volume of the fluid system 101 after the addition of the reference fluid ($V_s$) is measured, the known total volume ($V_t$) may also then be determined. Equation (7) may then be solved to determine the volume of an added reference gas ($V_s$).

In one or more embodiments, a proxy standard fluid may be used as the standard fluid injected in the fluid system 101. Proxy standard fluids may exhibit similar characteristics or optical responses as standard fluids, and may be close enough in their characteristics and/or optical responses that they may be used in place of a standard fluid. For example, heptane may be injected into the fluid system 101 as a proxy standard fluid for a standard fluid corresponding to saturates or like fluids. As will be appreciated, this may prove advantageous when a certain standard fluid is difficult to work with or otherwise obtain. For instance, some standard fluids may be dangerous or hazardous to handle, but a proxy standard fluid may not be dangerous to handle. Moreover, a standard fluid may be difficult to acquire or expensive to purchase, but a proxy standard fluid may be easy to acquire and less expensive. In at least one embodiment, a proxy standard fluid may be a combination of one or more fluids where the combination or mixture of the fluids is spectrographically the same or sufficiently close to the optical response of the desired standard fluid.

The computers and signal processors described herein, such as the signal processor 126, may include computer hardware used to implement the various computations and operations required to accurately detect a desired analyte of interest. The computer hardware may include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory associated with the signal processor 126. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium refers to any non-transitory medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

The computers and signal processors described herein may also include one or more peripheral devices, such as a monitor, a graphical user interface, a printer, or any other means whereby the computer or signal processor can be used to visualize the results of the presently-described methods and/or at least a portion of the processes described herein.

Embodiments disclosed herein include:

A. A measurement system that includes a fluid system that circulates a sample fluid exhibiting one or more unknown characteristics and being configured to receive a standard fluid that exhibits a known characteristic corresponding to at least one of the one or more unknown characteristics, an isolation cell fluidly coupled to the fluid system such that the sample fluid and a mixture of the sample fluid and the standard fluid are able to enter the isolation cell, an analyte-sensitive measurement device operably coupled to the isolation cell and having one or more sensors associated therewith, the analyte-sensitive measurement device being configured to analyze the sample fluid and the mixture and generate response signals corresponding to the one or more unknown characteristics of the sample fluid, and a signal processor communicably coupled to the analyte-sensitive measurement device and configured to receive and perform standard addition calculations on the response signals in order to determine a concentration of the one or more unknown characteristics of the sample fluid.

B. A method of circulating a sample fluid exhibiting one or more unknown characteristics within a fluid system, analyzing the sample fluid with an analyte-sensitive measurement device having one or more sensors associated therewith and generating with the analyte-sensitive measurement device a first response signal corresponding to the one or more unknown characteristics of the sample fluid, injecting a first known volume of a standard fluid into the fluid system, thereby generating a first mixture of the sample fluid and the standard fluid, the standard fluid exhibiting a known concentration of a known characteristic corresponding to at least one of the one or more unknown characteristics, analyzing the first mixture with the analyte-sensitive measurement device and generating with the analyte-sensitive measurement device a second response signal corresponding to the one or more unknown characteristics of the sample fluid, injecting a second known volume of the standard fluid into the fluid system and thereby generating a second mixture of the sample fluid and the standard fluid, analyzing the second mixture with the analyte-sensitive measurement device and generating with the analyte-sensitive measurement device a third response signal corresponding to the one or more unknown characteristics of the sample fluid, performing standard addition calculations on the first, second, and third response signals with a signal processor, and determining with the signal processor a concentration of the one or more unknown characteristics of the sample fluid based on the standard addition calculations.

Each of embodiments A and B may have one or more of the following additional elements in any combination: Element 1: wherein the fluid system further comprises one or more of a liquid charging system, a gas charging system, a temperature control system, and a pressure control system, wherein each system is configured to vary one or more operating conditions of the sample fluid. Element 2: wherein the one or more operating conditions include temperature, pressure, density, and chemical concentration of the sample fluid. Element 3: wherein the known characteristic and the one or more unknown characteristics comprise characteristics selected from the group consisting of chemical composition, phase, impurity content, pH, alkalinity, viscosity, density, ionic strength, total dissolved solids, salt content, porosity, opacity, bacteria content, total hardness, and state of matter. Element 4: wherein the analyte-sensitive measurement device is at least one of a gas chromatograph, a spectrometer, and an optical computing device that employs one or more integrated computational elements. Element 5: wherein the isolation cell defines an internal fluid flow path extending between two transparent windows and is configured to receive the sample fluid and the mixture therethrough. Element 6: wherein the one or more sensors comprise sensors selected from the group consisting of a thermal conductivity detector (TCD), a flame ionization detector (FID), a thermal detector, a semiconductor detector, a piezoelectric detector, a charge coupled device (CCD) detector, a video or array detector, a split detector, a photon detector, and photodiodes. Element 7: wherein the standard fluid is a proxy standard fluid exhibiting a similar optical response as a preferred standard fluid. Element 8: wherein the proxy standard fluid is a combination of two or more fluids, the combination of the two or more fluids being spectrographically similar to an optical response of the preferred standard fluid. Element 9: wherein the standard fluid is a gas chromatograph standard fluid.

Element 10: further comprising varying one or more operating conditions of the sample fluid circulating in the fluid system with one or more of a liquid charging system, a gas charging system, a temperature control system, and a pressure control system. Element 11: further comprising analyzing the sample fluid, the first mixture, and the second mixture in an isolation cell fluidly coupled to the fluid system. Element 12: wherein the analyte-sensitive measurement device is at least one of a gas chromatograph, a spectrometer, and an optical computing device that employs one or more integrated computational elements. Element 13: further comprising extracting an amount of the sample fluid from the fluid system, flashing one or more first gases out of the amount of the sample fluid, capturing the one or more first gases flashed from the amount of the sample fluid, and analyzing the one or more first gases with the analyte-sensitive measurement device for the presence of the one or more unknown characteristics. Element 14: further comprising extracting an amount of the first mixture from the fluid system, flashing one or more second gases out of the amount of the first mixture, capturing the one or more second gases flashed from the amount of the first mixture, and analyzing the one or more second gases with the analyte-sensitive measurement device for the presence of the one or more unknown characteristics. Element 15: wherein the known characteristic and the one or more unknown characteristics comprise characteristics selected from the group consisting of chemical composition, phase presence, impurity content, pH, alkalinity, viscosity, density, ionic strength, total dissolved solids, salt content, porosity, opacity, bacteria content, total hardness, and state of matter. Element 16: further comprising injecting one or more additional known volumes of the standard fluid into the fluid system to generate one or more additional mixtures of the sample fluid and the standard fluid, analyzing the one or more additional mixtures with the analyte-sensitive measurement device and generating with the analyte-sensitive measurement device one or more additional response signals corresponding to the one or more unknown characteristics of the sample fluid, and performing standard addition calculations on the one or more additional response signals with the signal processor to determine a more accurate concentration of the one or more unknown characteristics of the sample fluid. Element 17: further comprising adding a known concentration of a reference gas to the fluid system, and determining a volume of the reference gas added to the fluid system based on the concentration of the one or more unknown characteristics of the sample fluid.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
    circulating a sample fluid exhibiting one or more unknown characteristics within a fluid system;
    simulating a fluid found in a downhole environment by varying one or more operating conditions of the sample fluid flowing in the fluid system with one or both of a liquid charging system and a gas charging system and thereby charging the sample fluid as it circulates;
    analyzing the sample fluid with an analyte-sensitive measurement device having one or more sensors associated therewith and generating with the analyte-sensitive measurement device a first response signal corresponding to the one or more unknown characteristics of the sample fluid;
    injecting a first known volume of a standard fluid into the fluid system, thereby generating a first mixture of the sample fluid and the standard fluid, the standard fluid exhibiting a known concentration of a known characteristic corresponding to at least one of the one or more unknown characteristics;
    analyzing the first mixture with the analyte-sensitive measurement device to generate, with the analyte-sensitive measurement device, a second response signal corresponding to the one or more unknown characteristics of the sample fluid;
    injecting a second known volume of the standard fluid into the fluid system and thereby generating a second mixture of the sample fluid and the standard fluid;
    analyzing the second mixture with the analyte-sensitive measurement device to generate, with the analyte-sensitive measurement device, a third response signal corresponding to the one or more unknown characteristics of the sample fluid;
    performing standard addition calculations on the first, second, and third response signals with a signal processor; and
    determining with the signal processor a concentration of the one or more unknown characteristics of the sample fluid based on the standard addition calculations.

2. The method of claim 1, further comprising varying the one or more operating conditions of the sample fluid with one or both of a temperature control system and a pressure control system.

3. The method of claim 1, further comprising analyzing the sample fluid, the first mixture, and the second mixture in an isolation cell fluidly coupled to the fluid system.

4. The method of claim 1, wherein the analyte-sensitive measurement device is selected from the group consisting of a gas chromatograph, a spectrometer, and an optical computing device that employs one or more integrated computational elements.

5. The method of claim 1, further comprising:
extracting an amount of the sample fluid from the fluid system;
flashing one or more first gases out of the amount of the sample fluid;
capturing the one or more first gases flashed from the amount of the sample fluid; and
analyzing the one or more first gases with the analyte-sensitive measurement device for the presence of the one or more unknown characteristics.

6. The method of claim 5, further comprising:
extracting an amount of the first mixture from the fluid system;
flashing one or more second gases out of the amount of the first mixture;
capturing the one or more second gases flashed from the amount of the first mixture; and
analyzing the one or more second gases with the analyte-sensitive measurement device for the presence of the one or more unknown characteristics.

7. The method of claim 1, wherein the known characteristic and the one or more unknown characteristics comprise characteristics selected from the group consisting of chemical composition, impurity content, pH, alkalinity, ionic strength, total dissolved solids, salt content, and bacteria content.

8. The method of claim 1, further comprising:
injecting one or more additional known volumes of the standard fluid into the fluid system to generate one or more additional mixtures of the sample fluid and the standard fluid;
analyzing the one or more additional mixtures with the analyte-sensitive measurement device to generate, with the analyte-sensitive measurement device, one or more additional response signals corresponding to the one or more unknown characteristics of the sample fluid; and
performing standard addition calculations on the one or more additional response signals with the signal processor to determine a more accurate concentration of the one or more unknown characteristics of the sample fluid.

9. A measurement system, comprising:
a fluid system that circulates a sample fluid exhibiting one or more unknown characteristics and being configured to receive a standard fluid that exhibits a known characteristic corresponding to at least one of the one or more unknown characteristics, the fluid system including one or both of a liquid charging system and a gas charging system used to simulate a fluid found in a downhole environment by varying one or more operating conditions of the sample fluid flowing in the fluid system and thereby charge the sample fluid as it circulates;
an isolation cell fluidly coupled to the fluid system such that the sample fluid and a mixture of the sample fluid and the standard fluid are able to enter the isolation cell;
an analyte-sensitive measurement device operably coupled to the isolation cell and having one or more sensors associated therewith, the analyte-sensitive measurement device configured to analyze the sample fluid and the mixture and to generate response signals corresponding to the one or more unknown characteristics of the sample fluid; and
a signal processor communicably coupled to the analyte-sensitive measurement device and configured to receive and perform standard addition calculations on the response signals in order to determine a concentration of the one or more unknown characteristics of the sample fluid.

10. The measurement system of claim 9, wherein the fluid system further comprises one or both of a temperature control system and a pressure control system to vary the one or more operating conditions of the sample fluid.

11. The measurement system of claim 10, wherein the one or more operating conditions include temperature, pressure, density, and chemical concentration of the sample fluid.

12. The measurement system of claim 9, wherein the known characteristic and the one or more unknown characteristics comprise characteristics selected from the group consisting of chemical composition, impurity content, pH, alkalinity, ionic strength, total dissolved solids, salt content, and bacteria content.

13. The measurement system of claim 9, wherein the analyte-sensitive measurement device is selected from the group consisting of a gas chromatograph, a spectrometer, and an optical computing device that employs one or more integrated computational elements.

14. The measurement system of claim 9, wherein the isolation cell defines an internal fluid flow path extending between two transparent windows and is configured to receive the sample fluid and the mixture therethrough.

15. The measurement system of claim 9, wherein the one or more sensors comprise sensors selected from the group consisting of a thermal conductivity detector (TCD), a flame ionization detector (FID), a thermal detector, a semiconductor detector, a piezo-electric detector, a charge coupled device (CCD) detector, a video or array detector, a split detector, a photon detector, and photodiodes.

16. The measurement system of claim 9, wherein the standard fluid is a gas chromatograph standard fluid, which comprises a plurality of known hydrocarbon components and a known concentration of the known characteristic.

* * * * *